United States Patent
Kosegi et al.

(10) Patent No.: US 7,166,768 B2
(45) Date of Patent: Jan. 23, 2007

(54) WHISKER-MEDIATED TRANSFORMATION OF EMBRYOGENIC COTTON SUSPENSION CULTURES

(75) Inventors: Bridget D. Kosegi, Indianapolis, IN (US); Jeffrey R. Beringer, Carmel, IN (US); Asha Mehra Palta, Carmel, IN (US); Joseph F. Petolino, Zionsville, IN (US); Raghav Ram, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/391,707

(22) Filed: Mar. 19, 2003

(65) Prior Publication Data

US 2003/0188333 A1    Oct. 2, 2003

Related U.S. Application Data

(63) Continuation of application No. 09/975,238, filed on Oct. 11, 2001, now abandoned.

(60) Provisional application No. 60/239,511, filed on Oct. 11, 2000.

(51) Int. Cl.
*C12N 15/87* (2006.01)
(52) U.S. Cl. ............ 800/293; 800/298; 800/314; 435/468; 435/470
(58) Field of Classification Search .......... 800/278, 800/293, 298, 314; 435/419, 469, 468, 470
See application file for complete search history.

(56) References Cited

OTHER PUBLICATIONS

Sakhanokho H. et al. Crop Science, vol. 41; pp. 1235-1240.*
Frame et al., 1994, Plant Journal; vol. 6; pp. 941-948.*
Rajasekaran et al., Molecular Breeding, 1996 vol. 2, No. 4; pp. 307-319.*

* cited by examiner

*Primary Examiner*—Russell P. Kallis
(74) *Attorney, Agent, or Firm*—Donald Stuart

(57) ABSTRACT

Embryogenic cotton suspension cultures can be transformed by elongated, needle-like structures called "whiskers". The process comprises the agitation of cotton suspension cultures in the presence of DNA and whiskers, whereby DNA uptake and integration thereof is facilitated.

1 Claim, No Drawings

WHISKER-MEDIATED TRANSFORMATION OF EMBRYOGENIC COTTON SUSPENSION CULTURES

RELATED APPLICATIONS

This application is a continuation of prior application Ser. No. 09/975,238, filed Oct. 11, 2001, now abandoned, which claimed priority from Ser. No. 60/239,511 filed Oct. 11, 2000.

FIELD OF INVENTION

This invention relates to a method of using elongated, needle-like microfibers or "whiskers" to transform embryogenic cotton suspension cultures.

BACKGROUND OF THE INVENTION

Until recently, genetically manipulated plants were limited almost exclusively to those events created by application of classical breeding methods. Creation of new plant varieties by breeding was reserved primarily for the most agronomically important crops, such as corn, due to the cost and time needed to identify, cross, and stably fix a gene in the genome, thus creating the desired trait. In comparison, the advent of genetic engineering has resulted in the introduction of many different heterologous genes and subsequent traits into diverse crops including corn, cotton, soybeans, wheat, rice, sunflowers and canola in a more rapid manner. However, the intergression of a new transgene into elite germplasm is still quite a laborious task due to the tissue culturing and back-crossing needed to produce a commercially viable, elite, line.

Several techniques exist which allow for the introduction, plant regeneration, stable integration, and expression of foreign recombinant vectors containing heterologous genes of interest in plant cells. One such technique involves acceleration of microparticles coated with genetic material directly into plant cells (U.S. Pat. No. 4,945,050 to Cornell; U.S. Pat. No. 5,141,131 to DowElanco; and U.S. Pat. No. 5,538,877 and U.S. Pat. No. 5,538,880, both to Dekalb). This technique is commonly referred to as "microparticle bombardment" or "biolistics". Plants may also be transformed using Agrobacterium technology (U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to Max Planck, European Patent Applications 604662, 627752 and U.S. Pat. No. 5,591,616 to Japan Tobacco, European Patent Applications 0267159, and 0292435 and U.S. Pat. No. 5,231,019 all to Ciba-Geigy, U.S. Pat. Nos. 5,463,174 and 4,762,785 both to Calgene, and U.S. Pat. Nos. 5,004,863 and 5,159,135 both to Agracetus). Another transformation method involves the use of elongated needle-like microfibers or "whiskers" to transform maize cell suspension cultures (U.S. Pat. Nos. 5,302,523 and 5,464,765 both to Zeneca). In addition, electroporation technology has been used to transform plant cells from which fertile plants have been obtained (WO 87/06614 to Boyce Thompson Institute; U.S. Pat. Nos. 5,472,869 and 5,384,253 both to Dekalb; U.S. Pat. Nos. 5,679,558, 5,641,664, WO9209696 and WO9321335 to Plant Genetic Systems).

Despite all of the technical achievements, genetic transformation and routine production of transgenic plants in a commercially viable, elite, germplasm is still a laborious task. For example, microparticle bombardment, while capable of being used either on individual cells, cell aggregates, or plant tissues, requires preparing DNA-attached gold particles and optimization of an expensive and not yet widely available, "gun" apparatus. Techniques involving Agrobacterium are extremely limited because not all plant species or varieties within a given species are susceptible to infection by the bacterium. Electroporation techniques are not preferred due to the extreme difficulties and cost typically encountered in routinely making protoplast from different plant species and tissues thereof and the concomitant low viability and low transformation rate associated therewith.

Heterologous DNA can be introduced into regenerable plant cell cultures via whiskers-mediated transformation. While a general description of the process can be found in U.S. Pat. Nos. 5,302,523 and 5,464,765, both to Zeneca, no protocols have been published to date for whisker-mediated transformation of embryogenic cotton cultures.

WO 99/38979 describes whisker-mediated transformation of cotton callus, but does not disclose or suggest whisker-mediated transformation of embryogenic cotton suspension cultures.

SUMMARY OF THE INVENTION

The present invention relates to the production of fertile, transgenic, *Gossypium hirsutum* L. plants containing heterologous DNA preferably integrated into the chromosome of said plant and heritable by the progeny thereof.

Another aspect of the present invention relates to *Gossypium hirsutum* L. plants, plant parts, plant fibers, plant cells, plant cell aggregates, and seed derived from transgenic plants containing said heterologous DNA. The invention produces the fertile transgenic plants described herein by means of whisker-mediated cell perforation and heterologous DNA uptake, said whisker-mediated cell perforation being performed on embryogenic cotton suspension cultures.

Other aspects, embodiments, advantages, and features of the present invention will become apparent from the following specification.

DETAILED DESCRIPTION OF THE INVENTION

The following phrases and terms are defined below:

By "antisense" is meant an RNA transcript that comprises sequences complementary to a target RNA and/or mRNA or portions thereof and that blocks the expression of a target gene by interfering with the processing, transport, and/or translation of its primary transcript and/or mRNA. The complementarity may exist with any part of the target RNA, i.e., the 5' non-coding sequence, 3' non-coding sequence, introns, or the coding sequence. Antisense RNA is typically a complement (mirror image) of the sense RNA.

By "cDNA" is meant DNA that is complementary to and derived from a mRNA.

By "chimeric DNA construction" is meant a recombinant DNA containing genes or portions thereof from one or more species in either the sense or antisense orientation.

By "constitutive promoter" is meant promoter elements that direct continuous gene expression in all cell types and at all times (i.e., actin, ubiquitin, CaMV 35S, 35T, and the like).

By "cosuppression" is meant the introduction of a foreign gene having substantial homology to an endogenous gene, and in a plant cell causes the reduction in activity of the foreign gene and/or the endogenous gene product. Cosuppression can be sometimes achieved by introducing into said plant cell either the promoter sequence, the 5' and/or 3' ends, introns or the coding region of a gene.

By "developmental specific" promoter is meant promoter elements responsible for gene expression at specific plant developmental stages, such as in early or late-embryogenesis and the like.

By "enhancer" is meant nucleotide sequence elements which can stimulate promoter activity such as those from maize streak virus (MSV), alfalfa mosaic virus (AMV), alcohol dehydrogenase intron 1 and the like.

By "expression" as used herein, is meant the transcription of enzymatic nucleic acid molecules, mRNA, and/or the antisense RNA inside a plant cell. Expression of genes also involves transcription of the gene and may or may not involve translation of the mRNA into precursor or mature proteins.

By "foreign" or "heterologous gene" is meant a gene having a DNA sequence that is not normally found in the host cell, but is introduced by whisker-mediated transformation.

By "gene" is meant to include all genetic material involved in protein expression including chimeric DNA constructions, genes, plant genes and portions thereof.

By "genome" is meant genetic material contained in each cell of an organism and/or virus.

By "inducible promoter" is meant promoter elements which are responsible for expression of genes in response to a specific signal, such as: physical stimuli (heat shock genes); light (RUBP carboxylase); hormone (Em); metabolites, stress and the like.

By "modified plant" is meant a plant wherein the mRNA levels, protein levels or enzyme specific activity or a particular protein have been altered relative to that seen in an unmodified plant. Modification can be achieved by methods such as antisense, cosuppression, or over-expression.

By "plant tissues" is meant organized tissues including but not limited to meristems, embryos, pollen, cotyledons, germ cells, and the like.

By "promoter regulatory element" is meant nucleotide sequence elements within a nucleic acid fragment or gene which controls the expression of that nucleic acid fragment or gene. Promoter sequences provide the recognition for RNA polymerase and other transcriptional factors required for efficient transcription. Promoter regulatory elements from a variety of sources can be used efficiently in plant cells to express sense and antisense gene constructs. Promoter regulatory elements are also meant to include constitutive promoters, tissue-specific promoters, developmental-specific promoters, inducible promoters and the like. Promoter regulatory elements may also include certain enhancer sequence elements that improve transcriptional or translational efficiency.

By "tissue-specific" promoter is meant promoter elements responsible for gene expression in specific cell or tissue types, such as the leaves or seeds (i.e., zein, oleosin, napin, ACP, globulin and the like).

By "whiskers" is meant elongated needle-like bodies capable of being produced from numerous substances as described in "The Condensed Chemical Dictionary, Seventh Edition, Ed. Arthur & Elizabeth Rose, Reinhold Publishing Corp., New York (1966). The invention is not meant to be limited to the material from which the whiskers are made but instead is meant to define a needle-like shaped structure wherein said whisker is smaller than the cell for which it is intended to be used in the transformation thereof. It is within the scope of this invention for whiskers to be shaped in a manner whereby DNA entry into a cell is facilitated. It is also intended that the scope of said invention include any material having a needle-like shape, said needle-like shaped material being able to perforate a plant cell with or without cell walls and thus facilitate DNA uptake and plant cell transformation. It is also intended that the scope of this invention not include microinjection techniques, such as wherein a DNA molecule is inserted into a cell by passing said DNA through an orifice intrinsic to a needle, said needle being first inserted into said cell. Preferably, whiskers are metal or ceramic needle-like bodies, with those most preferred being made of either silicon carbide or silicon nitride and being 30×0.5 μm to 10×0.3 μm in size.

By "whisker-mediated transformation" is meant the facilitation of DNA insertion into plant cells and/or plant tissues by whiskers and expression of said DNA in either a transient or stable manner.

In producing plant cell lines, tissues of interest are aseptically isolated and placed onto solid initiation medium whereby processes associated with cell differentiation and specialization occurring in organized plant cell tissues are disrupted, thus resulting in said tissues becoming dedifferentiated. Typically, initiation medium is solidified by adding agar or the like because callus cannot be readily initiated in liquid medium. Media are typically based on the N6 salts of Chu et al., (1978, Proc. Symp. Plant Tissue Culture, Peking Press, p 43–56) being supplemented with sucrose, vitamins, minerals, amino acids, and in some cases, synthetic hormones. However, callus tissues can also proliferate on media derived from the MS salts of Murashige and Skoog, (1962 Physiol. Plant. 15: 473–497). Cultures are generally maintained in a dark, sterile environment at about 28° C.

The heterologous DNA used for transformation herein may be circular, linear, double-stranded or single-stranded. Generally, said DNA is a recombinant vector plasmid and contains coding regions therein which serve to promote expression of the heterologous gene of interest as well as provide a selectable marker whereby those tissues containing said gene can be identified. Preferably, these recombinant vectors are capable of stable integration into the plant genome where selection of transformed plant lines is made possible by having said selectable marker expression driven either by constitutive, tissue-specific, or inducible promoters included therein. One variable present in a heterologous DNA is the choice of the chimeric gene. Chimeric genes, either in the sense or antisense orientation, are expressed in plant cells under control of a constitutive, tissue-specific, developmental, or inducible promoter and the like. Preference for a particular chimeric gene is at the discretion of the artisan; however, chimeric genes can be, but are not limited to, those from plants, animals, or bacteria and the like and can used to express proteins either not found in a non-transformed cell or found in a transformed cell. Chimeric genes can be also used for, but are not limited to, up-regulation or down-regulation of an endogenous gene of interest. The chimeric gene may be any gene that it is desired to express in plants. Particularly useful genes are those that confer tolerance to herbicides, insects, or viruses, and genes that provide improved nutritional value or processing characteristics of the plant. Examples of suitable agronomically useful genes include the insecticidal gene from *Bacillus thuringiensis* for conferring insect resistance and the 5'-enolpyruvyl-3'-phosphoshikimate synthase (EPSPS) gene and any variant thereof for conferring tolerance to glyphosate herbicides. As is readily understood by those skilled in the art, any agronomically important gene conferring a desired trait can be used.

Another variable is the choice of a selectable marker. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialophos); imidazolinones, sulfonylureas and triazolopyrimidine herbicides, such as chlorsulfuron; bromoxynil, dalapon and the like.

In addition to a selectable marker, it may be desirable to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Weising et al. Ann. Rev. Genetics, 22, 421 (1988), which is incorporated herein by reference. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987 Biochem. Soc. Trans. 15, 17–19) to identify transformed cells.

Another variable is a promoter regulatory element. In addition to plant promoter regulatory elements, promoter regulatory elements from a variety of sources can be used efficiently in plant cells to express heterologous genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see PCT/US96/1682; WO 97/13402 published Apr. 17, 1997) and the like may be used. Plant promoter regulatory elements include but are not limited to ribulose-1,6-bisphosphate (RUBP) carboxylase small subunit (ssu), beta-conglycinin promoter, phaseolin promoter, ADH promoter, heat-shock promoters and tissue specific promoters.

Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, stability of the mRNA and the like. Such elements may be included in the DNA as desired to obtain optimal performance of the transformed DNA in the plant. Typical elements include but are not limited to Adh-intron 1, the alfalfa mosaic virus coat protein leader sequence, the maize streak virus coat protein leader sequence, as well as others available to a skilled artisan.

Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and may also be used.

Promoter regulatory elements may also be active during a certain stage of the plants' development as well as active in specific plant tissues and organs. Examples of such include but are not limited to pollen-specific, embryo specific, corn silk specific, cotton fiber specific, root specific, seed endosperm specific promoter regulatory elements and the like. Under certain circumstances it may be desirable to use an inducible promoter regulatory element responsible for expression of genes in response to a specific signal, such as: physical stimulus (heat shock genes); light (RUBP carboxylase); hormone (Em); metabolites; and stress. Other desirable transcription and translation elements functional in plants may also be used. Numerous plant-specific gene transfer vectors are known and available to the skilled artisan.

In whisker-mediated transformation, DNA uptake into plant material is facilitated by very small, elongated, needle-like particles comprised of a biologically inert material. When said particles are agitated in the presence of DNA and plant cell lines, one or more of the particles produce small punctures in the regenerable plant cell aggregates thereby allowing said aggregates to uptake the DNA. Cells which have taken up the DNA are considered to be transformed. Some transformed cells stably retain the introduced DNA and express it.

The elongated needle-like particles used in plant cell transformation are termed "whiskers" and are preferably made of a high density material such as silicon carbide or silicon nitride; however, any material having a needle-like structure wherein the size of said structure is smaller than the cell intended to be transformed is within the scope of the invention. More preferably, whiskers are made of silicon carbide and are either Silar SC-9 or Alfa Aesar as described herein.

For transformation, whiskers are typically placed in a small container, such as a conical or microfuge tube and the like, wherein is placed a mixture comprising the DNA construct of interest and embryogenic cotton suspension culture. Thereafter, the container is sealed and agitated. Unlike particles used in biolistic transformation of plant tissue (Sanford et al., 1990 Physiol. Plantarum, 79:206–209; and U.S. Pat. No. 5,100,712), whiskers do not require any special pretreatment with DNA carriers or precipitants prior to use such as $CaCl_2$, spermidine, sheared salmon sperm DNA and the like.

Agitation time used in the transformation process can vary and is typically from between about 10 sec to about 160 sec. The amount of whiskers added per transformation can also vary from between about 1 mg to about 4 mg per tube. An inverse relationship is observed between the amount of whiskers added and the agitation time needed to obtain optimal transformation. Therefore, the amount of whiskers added and the agitation time needed to achieve transformation is determinable by one having skill in the art. In addition, the volume of liquid medium added can vary from about 200 μL to about 1000 μL, with about 200 μL being preferred. Moreover, the amount of heterologous DNA added can vary from a preferred amount of about 10 μL to about 100 μL of 1 mg/mL solution. The volume of DNA added is not as critical of factor to the invention as disclosed herein as the final DNA concentration. However, preferred final DNA concentrations are from about 0.03 μg/μL to about 0.14 μg/μL. The scope of the present invention is not intended to be limited to said container size, the amount or concentration of heterologous DNA added, the volume of heterologous DNA added, the amount of the liquid medium added, the amount of suspension culture added or the amount of whiskers added as disclosed herein. The scope of the invention is also not intended to be limited by the instrumentation used to agitate the mixture or whether agitation is accomplished by manual or mechanical means.

Once the plant cell lines have been perforated and the heterologous DNA has entered therein, it is necessary to identify, propagate, and select those cells which not only contain the heterologous DNA of interest but are also capable of regeneration. Said cells and plants regenerated therefrom can be screened for the presence or absence of the heterologous DNA by various standard methods including but not limited to assessment of reporter gene expression. Alternatively, transmission of a selectable marker gene along with or as part of the heterologous DNA allows those cells containing said DNA to be identified by use of a selective agent.

Selection of only those cells containing and expressing the heterologous DNA of interest is a critical step in production of fertile, transgenic plants. Selection conditions must be chosen in such a manner as to allow growth of transformed cells while inhibiting growth of untransformed cells, which initially, are far more abundant. In addition, selection conditions must not be so severe as to cause transformed cells to lose their plant regenerability, future viability or fertility. A skilled artisan can easily determine appropriate conditions for selecting transformed cells expressing a particular selectable marker by performing growth inhibition curves. Growth inhibition curves are generated by plotting cell growth versus selective agent concentration. Typically, selective agent concentrations are set at a concentration whereby almost all non-transformed cells are growth inhibited but yet are not killed. Preferred are selective agent concentrations wherein 90–99% of non-transformed cells are growth inhibited but yet not killed. Most preferred are selective agent concentrations wherein 97–99% of non-transformed cells are growth inhibited but yet not killed.

Transformed cells transferred and exposed to selective agents are generally incubated on solid or liquid medium supportive of growth. The medium preferred for each type of tissue has been well defined in the art. After initial exposure to selective agents, the cells are transferred periodically to fresh medium while maintainina selective agent concentrations. After transformed cell mass has essentially doubled in size, masses showing the most growth and appearing to be healthy are selected and transferred to fresh medium having-selective agent concentrations wherein non-transformed cells will be killed. Repeated selection and transference of growing cells to fresh medium result eventually in a selected group of cells comprised almost exclusively of transformed cells containing the heterologous DNA of interest.

Regeneration, while important to the present invention, may be performed in any conventional manner available to the skilled artisan. If cells have been transformed with selectable marker gene, the selective agent may be incorporated into the regeneration media to further confirm that the regenerated plantlets are transformed. After subsequent weeks of culturing, regenerated plantlet immune to the selective agent can be transferred to soil and grown to maturity.

Cells and plant derived therefrom can be identified as transformants by phenotypic and/or genotypic analysis. For example, if an enzyme or protein is encoded by the heterologous DNA, enzymatic or immunological assays specific for the particular enzyme or protein can be used. Other gene products may be assayed by using suitable bioassays or chemical assays. Other techniques include analyzing the genomic component of the plant using methods as described by Southern ((1975) J. Mol. Biol., 98:503–517), polymerase chain reaction (PCR) and the like.

Plants regenerated from transformed cells are referred to as the RO generation or RO plants. Seed produced by various sexual crosses from plants of this generation are referred to as R1 progeny. R1 seed are then germinated to produce R1 plants. Successful transmission and inheritance of heterologous DNA to R1 plants and beyond should be confirmed using the methods described herein.

Particular embodiments of this invention are further exemplified in the Examples. However, those skilled in the art will readily appreciate that the specific experiments detailed are only illustrative of the invention as described more fully in the claims which follow thereafter.

EXAMPLE 1

Initiation of Embryogenic Cotton Suspension Cultures

Embryogenic cotton suspension cultures were established from embryogenic callus, which in turn was derived from cotyledonary segments. Seeds of cotton (*Gossypium hirsutum* L.) were treated with 95% Ethanol for 1 minute, rinsed, and then surface-sterilized with 50% Clorox for 20 minutes. The seeds were washed 3 times with sterile distilled water and planted on MS medium (Murashige and Skoog, 1962) containing 2% sucrose and 0.8% Noble agar. The cultures were maintained at 28° C. in the light with a photoperiod of 16 hrs light and 8 hrs dark. Seven to ten days after germination, the cotyledon segments (3 mm square) were placed on callus induction medium (Finer, 1988). The callus was maintained on MS medium with 2 mg/l NAA, 1 mg/l Kinetin, 3% glucose, and 0.8% agar for 3 months with a transfer to fresh medium every 3 weeks. Embryogenic callus was obtained after 4–8 weeks culture on the basal agar media. Embryogenic suspensions were developed from the embryogenic callus tissue and were maintained in Ep media (MS salts, modified B5 vitamins, 4.42 mg/l 2,4-D and 2% sucrose. Subculture occurred every 14 days and was accomplished by pipetting 0.25 ml pcv (packed cell volume) into an autoclaved 125 ml flask (Bellco #2543-00125) containing 35 ml Ep media. The flask was then capped with a stainless steel closure (Bellco #2005-00025) and wrapped with Parafilm™. A variety of independently derived lines from genotypes GC 510, Coker 310, and Coker 312 were utilized in this work.

EXAMPLE 2

Construction of the Plasmids

The plant expression vector, pDAB219 (8008 bp), contained a cauliflower mosaic virus 35S promoter (Sanders et al., 1987. Nucleic Acids Res. 15(4) 543–1558) driving the β-glucuronidase (GUS) gene described by Jefferson (1987, Plant Mol. Biol. Rep. 5, 387–405). The transcription of the GUS gene was terminated by the 3' end untranslated region (3' UTR) of nopaline synthetase (NOS) gene from *Agrobacterium tumefaciens* (Bevan et al., 1983, Nuclei Acids Res. 11(2), 369–385). Vector pDAB219 also contained the 35S promoter driving the *Streptomyces hygroscopicus* bar gene that conferring resistance to herbicide bialaphos (Thompson et al., 1987, EMBO J. 6, 2519–2523). The transcription termination of the bar gene was terminated by NOS 3' UTR. This cassette was located downstream of the GUS expression cassette. These 2 plant gene expression cassettes were harbored in the plasmid backbone of pUC19 (Yanish-Perron et al., 1985, Gene 33:103–119).

The plant expression vector p179-3, contained Super-Mas1 promoter driving GUS. The transcription of GUS was terminated by NOS 3' UTR. This expression cassette was harbored in the plasmid backbone of pUC19.

The plant expression vector pDAB418, contained a Ubi1 promoter from maize Ubiquitin1 gene (Quail et al., 1989, U.S. Pat. No. 5,614,339) driving the GUS. The transcription of GUS was terminated by NOS 3' UTR. Vector pDAB219 also contained the Ubi1 promoter driving the bar gene. Transcription of the bar gene was terminated by NOS 3' UTR. The expression cassette was located on the downstream of the GUS expression cassette. Both expression cassettes were harbored in the plasmid backbone of pUC19.

EXAMPLE 3

Whisker Preparation and Optimization for Transient Expression

Embryogenic cotton suspension material was placed into liquid Ep media with osmoticants (36.4 g/l Mannitol and 36.4 g/l Sorbitol) and allowed to incubate on a rotary shaker at 150 rpm, at 28° C. in the light for approximately 4 hours. Ahead of time, a sterilized sample of silicon carbide whiskers was prepared as follows: A small hole was made in the top of a 2.0 ml Eppendorf tube and then covered with a piece of tape. The tube was weighed and 60–80 mg of dry whiskers (Advanced Composite, Greer, S.C.) were placed inside. [Note: Gloves and a respirator should be worn, and the transfer done in a fume hood with damp paper towels to immobilize any spilled whiskers.] The tube was weighed again, then placed in a Magenta™ box and autoclaved for 30 minutes. The pretreated embryogenic cotton suspension was divided into 0.125 ml packed cell volume (pcv) samples and placed into 17×100 mm culture tubes (Falcon 2059). Using a wide-bore pipette tip, 20 μg of DNA solution (1.0 μg/μl in TE buffer) was added along with 500 μl of liquid Ep media with osmoticants to each tube. Immediately before use, a 4% (i.e., 40 mg/ml) whisker suspension was prepared by adding an appropriate amount of liquid Ep media with osmoticants to an autoclaved whisker sample and vortexing for 60 seconds to mix thoroughly. Using a filtered wide-bore pipette tip, 100 μl of 4% whisker suspension was added to the cotton suspension/DNA mixture and agitated using a Caulk 'Vari-Mix II' dental amalgamator (Estrada Dental Co., Cucamunga, Calif.) modified to hold a 14 ml Falcon tube. Samples are agitated for 20 seconds on medium speed (setting 2). The embryogenic cotton suspension/DNA/whisker mixture was then transferred to fresh Ep media without osmoticants and was placed on a rotary shaker at 150 rpm at 28° C. in 16 hours of light.

For transient studies, GUS expression was analyzed by histochemical assay. The suspensions were allowed to recover for 2 days. Following the recovery period, the suspension tissue was placed into GUS assay solution and allowed to incubate in the dark for 48 hours at 37° C. After the GUS developed, the entire sample was pipetted onto a piece of filter paper upon which a grid has been drawn. The grid helps to keep track of which areas of the sample have been counted. The entire sample was examined and all blue expression units were counted, recorded, and analyzed.

Transient Results. Several transient experiments were done initially and throughout the project to establish favorable conditions for gene transfer. Six of the parameters tested yielded no significant differences in transient expression of the GUS reporter gene. A comparison of treatment vessels showed no significant difference between a 14 ml culture tube (Falcon 352059), a 6 ml culture tube (Falcon 352063), and a 2 ml Eppendorf tube (see Table 1). However, the highest Gus expression was obtained with 14 ml Falcon tubes and these were used in all subsequent experiments.

TABLE 1

Transient GUS Expression in Various Treatment Vessels

| Cell Line | Falcon Tube (14 ml) | Small Falcon Tube (6 ml) | Eppendorf Tube (2 ml) |
|---|---|---|---|
| C-49-B | 89 | 297 | 152 |
| C-49-B | 406 | 234 | 294 |
| C-49-B | 470 | 225 | 134 |
| Mean GEUs | 321.7 | 252.0 | 193.3 |
| Standard Deviation | 166.6 | 32.0 | 71.6 |

Similarly, no significant difference was observed between 10 μg, 20 μg, and 30 μg of DNA added to each sample or between the high 2, medium 2, and low 2 settings for agitation speed on the Vari-Mix™ (see Tables 2 and 3 respectively).

TABLE 2

Transient GUS Expression Using Various Amounts of DNA

| Cell line | 10 μg DNA | 20 μg DNA | 30 μg DNA |
|---|---|---|---|
| C-49-B | 887 | 981 | 615 |
| C-49-B | 458 | 515 | 519 |
| C-49-B | 296 | 433 | 363 |
| C-49-B | 354 | 385 | 302 |
| Mean GEUs | 498.8 | 578.5 | 449.8 |
| Standard Deviation | 231.5 | 237.0 | 124.0 |

TABLE 3

Transient GUS Expression Using Various Amounts of a 4% Whisker Suspension

| Cell line | 50 μl Whiskers | 100 μl Whiskers | 200 μl Whiskers | 300 μl Whiskers |
|---|---|---|---|---|
| C-49-B | 568 | 981 | 359 | 631 |
| C-49-B | 506 | 515 | 905 | 921 |
| C-49-B | 629 | 433 | 473 | 251 |
| C-49-B | 286 | 385 | 429 | 990 |
| Mean GEUs | 497.3 | 578.5 | 541.5 | 698.3 |
| Standard Deviation | 129.5 | 237.0 | 213.8 | 291.2 |

A comparison of three different agitation speeds on the Vari-Mix™ showed no significant difference among them. Zero DNA samples are controls, which are whisker treated but receive no DNA.

TABLE 4

Transient GUS ExFression in Samples Agitated at Three Different Speeds

| Van-mix speeds: | Low 2 | Medium 2 | High 2 |
|---|---|---|---|
| sample 1 | 78 | 96 | 89 |
| sample 2 | 50 | 93 | 97 |
| sample 3 | 55 | 120 | 109 |
| sample 4 | 84 | 67 | 74 |
| sample 5 | 78 | 131 | 79 |
| sample 6 | 95 | 102 | 74 |
| Zero DNA | 0 | 0 | 0 |
| Mean GEU's | 73.3 | 101.5 | 87.0 |
| Standard Deviation | 15.8 | 20.4 | 12.8 |

An osmotic solution is used in three different places in the transformation protocol. Tissue was pretreated in an osmoticant, 0.5 ml of osmotic solution added to each sample, and the whisker suspension was made up with osmotic solution. Three different osmotic solutions are compared in Table 5.

TABLE 5

Transient GUS Expression in Samples Treated with Three Different Osmotic Solutions

| Sample # | Ep plus 36.4 g/l mannitol and 36.4 g/l sorbitol | FGI-12% sucrose (Sunflower Media) | Ep plus 12% sucrose |
|---|---|---|---|
| sample 1 | 405 | 586 | 308 |
| sample 2 | 410 | 328 | 322 |
| sample 3 | 363 | 451 | 362 |
| sample 4 | 527 | 344 | 373 |
| sample 5 | 646 | 306 | 367 |
| sample 6 | 457 | 362 | 359 |
| sample 7 | 441 | 397 | 393 |
| sample 8 | 678 | 578 | 359 |
| sample 9 | 535 | 418 | 336 |
| sample 10 | 466 | 520 | 441 |
| Zero DNA | 0 | 0 | 0 |
| Mean GEU's | 492.8 | 429.0 | 362.0 |
| Standard Deviation | 98.4 | 96.9 | 35.4 |

Ep is the standard growth and maintenance media for cotton suspensions. FGI is a similar liquid media with glutamine and slightly higher concentrations of 2,4 D. Two different osmotic pretreatment times were also tested. Table 6 summarizes the results of an experiment, which included three variables: suspension line and genotype, osmotic pretreatment time, and osmoticant. No differences could be seen between the osmoticants or the pretreatment times, however some differences could be seen between the two suspension lines used in this experiment. The suspension line C-49-B is from the GC 510 genotype and 58-C-BY is a Coker 310 line.

TABLE 6

Transient GUS Expression in Samples Treated with Two Different Osmotic Pretreatment Times

| Sample # | 58-C-BY tissue in Ep + 12% sucrose for 15 min | C-49-B tissue in Ep + 12% sucrose for 15 min | C-49-B tissue in EpO for 4 hrs | 58-C-BY tissue in EpO for 4 hrs |
|---|---|---|---|---|
| sample 1 | 150 | 203 | 162 | 44 |
| sample 2 | 39 | 124 | 153 | 53 |
| sample 3 | 70 | 88 | 140 | 86 |
| sample 4 | 39 | 95 | 139 | 49 |
| sample 5 | 108 | 74 | 183 | 57 |
| sample 6 | 64 | 117 | 79 | 73 |
| sample 7 | 68 | 118 | 160 | 65 |
| sample 8 | 37 | 140 | 156 | 35 |
| sample 9 | 78 | 87 | 189 | 37 |
| sample 10 | 54 | 128 | 246 | 35 |
| Zero DNA | 0 | 0 | 0 | 0 |
| Mean GEU's | 70.7 | 117.4 | 160.7 | 53.4 |
| Standard Deviation | 33.5 | 34.9 | 40.3 | 16.3 |

Eight other parameters did yield significant differences in transient GUS expression between treatments. Table 7 illustrates a comparison of five different tissue amounts. It appears as though GUS expression falls off after 0.12 ml pcv, but when these data are expressed as the amount of GUS expression per 1 ml pcv of whisker treated suspension tissue, it can be seen that the two smallest tissue amounts yield roughly equivalent GUS expression. However, tissue amount is not as limiting a factor in these experiments as the number of samples that can be treated. The most important measure is the amount of GUS expression per sample. Therefore 0.12 ml pcv was the chosen amount of tissue.

TABLE 7

Transient GUS Expression in Two Experiments Using Various Amounts of Tissue

| Cell Line | 1.0 ml pcv | 0.5 ml pcv | 0.25 ml pcv | 0.12 ml pcv | 0.06 ml pcv |
|---|---|---|---|---|---|
| C-49-B | 177 | 415 | 339 | | |
| C-49-B | 147 | 149 | 232 | | |
| C-49-B | 213 | 98 | 504 | | |
| C-49-B | 117 | 268 | 175.5 | | |
| C-49-B | | | 431 | 368 | 172 |
| C-49-B | | | 209 | 285 | 156 |
| C-49-B | | | 371 | 377 | 218 |
| C-49-B | | | | 400 | 216 |
| Mean GEUs | 163.5 | 232.5 | 323.1 | 357.5 | 190.5 |
| Standard Deviation | 35.6 | 122.1 | 113.4 | 43.5 | 27.1 |

A dramatic difference in transient expression was seen in a side by side comparison of SiC fibers produced by two different companies. Table 8 displays the results of an experiment comparing whiskers from Alfa Aesar with those from Advanced Composite.

TABLE 8

Transient GUS Expression Produced by Two Whisker Types

| Cell line | Alfa Aesar with 0.25 ml pcv | Advanced Composite with 0.25 ml pcv | Alfa Aesar with 0.12 ml pcv |
| --- | --- | --- | --- |
| C-49-B | 190 | 471 | 103 |
| C-49-B | 245 | 500 | 256 |
| C-49-B | 149 | 638 | 200 |
| C-49-B |  | 642 | 249 |
| Mean GEUs | 194.7 | 562.8 | 202.0 |
| Standard Deviation | 39.3 | 77.9 | 61.1 |

The device chosen to agitate samples also proved to be significant. A comparison of samples agitated in 14 ml culture tubes on the Vari-Mix™ and samples agitated in 2 ml Eppendorf tubes on a Vortex Genie 2® mixer with a TurboMix™ attachment (Scientific Industries, 70 Orville Drive, Bohemia, N.Y. 11716 USA) showed that the three dimensional motion of the Vari-Mix™ yielded markedly higher transient expression (see Table 9).

TABLE 9

Transient GUS Expression in Samples Agitated by Two Different Devices

| Treatment | Vari-Mix, 20 sec, Medium 2 | Turbomix, 60 sec, full speed |
| --- | --- | --- |
| sample 1 | 129 | 17 |
| sample 2 | 119 | 16 |
| sample 3 | 166 | 10 |
| sample 4 | 157 | 24 |
| sample 5 | 149 | 13 |
| sample 6 | 144 | 11 |
| Zero DNA | 0 | 0 |
| Mean GEU's | 144.0 | 15.2 |
| Standard Deviation | 16.0 | 4.7 |

Shorter agitation times were found to be more effective than longer agitation times.

TABLE 10

Transient GUS Expression in Samples Agitated for Various Times

| Van-mix times: | 5 sec | 20 sec | 40 sec | 60 sec |
| --- | --- | --- | --- | --- |
| sample 1 | 165 | 119 | 82 | 73 |
| sample 2 | 196 | 160 | 96 | 74 |
| sample 3 | 164 | 153 | 93 | 54 |
| sample 4 | 173 | 184 | 91 | 52 |
| sample 5 | 184 | 147 | 108 | 107 |
| sample 6 | 161 | 212 | 100 | 52 |
| Zero DNA | 0 | 0 | 0 | 0 |
| Mean GEU's | 173.8 | 162.5 | 95.0 | 68.7 |
| Standard Deviation | 12.5 | 29.3 | 8.0 | 19.5 |

Another factor, which has great influence over transient GUS expression, is the cell line used in the transformation experiment. Four experiments were conducted to compare the transformability of several lines. Suspension lines with the prefix 57 are Coker 312 genotype and the prefix 58 designates a Coker 310 genotype. All other lines are GC 510 genotype. Each experiment consisted of six replicates and one negative control (to which no DNA was added). The transformation parameters were the same as those listed for the promoter comparison experiments. The second experiment (table 12) is a repeat of the first (table 11).

TABLE 11

Transient GUS Expression in Various EmbryogenicCotton Suspension Lines

| cell line | 70-C-145 | 65-C-137 | 70-C-157 | 65-C-140 | C-49-B |
| --- | --- | --- | --- | --- | --- |
| sample 1 | 78 | 25 | 17 | 20 | 116 |
| sample 2 | 51 | 35 | 21 | 12 | 145 |
| sample 3 | 27 | 57 | 18 | 13 | 63 |
| sample 4 | 39 | 38 | 16 | 10 | 128 |
| sample 5 | 73 | 44 | 27 | 11 | 71 |
| sample 6 | 65 | 37 | 26 | 24 | 20 |
| Zero DNA | 0 | 0 | 0 | 0 | 0 |
| Mean GEU's | 55.5 | 39.3 | 20.8 | 15.0 | 90.5 |
| Standard Deviation | 18.3 | 9.7 | 4.3 | 5.2 | 43.1 |

TABLE 12

Transient GUS Expression in Various Embryogenic Cotton Suspension Lines

| cell line | 70-C-145 | 65-C-137 | 70-C-157 | 65-C-140 | C-49-B |
| --- | --- | --- | --- | --- | --- |
| sample 1 | 40 | 55 | 118 | 14 | 101 |
| sample 2 | 71 | 65 | 103 | 8 | 122 |
| sample 3 | 54 | 39 | 94 | 23 | 214 |
| sample 4 | 67 | 65 | 118 | 14 | 121 |
| sample 5 | 82 | 45 | 105 | 6 | 190 |
| sample 6 | 73 | 30 | 122 | 15 | 164 |
| Zero DNA | 0 | 0 | 0 | 0 | 0 |
| Mean GEU's | 64.5 | 49.8 | 110.0 | 13.3 | 152.0 |
| Standard Deviation | 13.8 | 13.0 | 10.0 | 5.5 | 40.6 |

TABLE 13

Transient GUS Expression in Various Embryogenic Cotton Suspension Lines

| cell line | C-49-B | 78-C-252 | 58-C-BY | 57-C-Z | 70-C-159 |
| --- | --- | --- | --- | --- | --- |
| sample 1 | 0 | 99 | 64 | 103 | 47 |
| sample 2 | 0 | 113 | 90 | 84 | 34 |
| sample 3 | 0 | 122 | 89 | 70 | 32 |
| sample 4 | 0 | 120 | 108 | 64 | 73 |
| sample 5 | 0 | 81 | 131 | 16 | 19 |
| sample 6 | 0 | 65 | 115 | 84 | 47 |
| Zero DNA | 0 | 0 | 0 | 0 | 0 |
| Mean GEU's | 0.0 | 100.0 | 99.5 | 70.2 | 42.0 |
| Standard Deviation | 0.0 | 21.0 | 21.5 | 27.2 | 16.9 |

TABLE 14

Transient GUS Expression in Various Embryogenic Cotton Suspension Lines

| cell line | C-49-B | 70-C-159 | C-57-BV | 58-C-BQ |
| --- | --- | --- | --- | --- |
| sample 1 | 213 | 83 | 112 | 67 |
| sample 2 | 282 | 70 | 93 | 112 |
| sample 3 | 222 | 40 | 130 | 135 |
| sample 4 | 163 | 75 | 71 | 85 |
| sample 5 | 144 | 62 | 87 | 104 |
| sample 6 | 186 | 47 | 90 | 49 |
| Zero DNA | 0 | 0 | 0 | 0 |

TABLE 14-continued

Transient GUS Expression in Various Embryogenic Cotton Suspension Lines

| cell line | C-49-B | 70-C-159 | C-57-BV | 58-C-BQ |
|---|---|---|---|---|
| Mean GEU's | 201.7 | 62.8 | 97.2 | 92.0 |
| Standard Deviation | 44.8 | 15.2 | 19.0 | 28.6 |

A post-treatment in an osmotic solution was tried as part of the recovery period. Results in table 15 show that no osmotic post-treatment is the most effective treatment. This experiment was conducted with a 15 minute pretreatment in Ep+12% sucrose.

TABLE 15

Transient GUS Expression in Samples Placed in Various Osmotic Post-treatments

| Treatment: | No Osmotic Posttreatment | 1 hour Osmotic Posttreatment | 3 day Osmotic Posttreatment |
|---|---|---|---|
| sample 1 | 493 | 221 | 404 |
| sample 2 | 460 | 151 | 273 |
| sample 3 | 505 | 378 | 270 |
| sample 4 | 625 | 342 | 468 |
| Zero DNA | 0 | 0 | 0 |
| Mean GEU's | 520.8 | 273.0 | 353.8 |
| Standard Deviation | 62.4 | 91.3 | 85.3 |

Finally, a change in protocol yielded an increase in GUS expression in one transient experiment. The protocol change entailed a "one at a time" treatment whereby DNA was added to each tube last, that tube was agitated and the tissue returned to liquid Ep media, before DNA was added to the next sample and the process repeated.

TABLE 16

Transient GUS Expression in Samples Treated with a Modified Protocol

| Sample # | Standard Protocol | "One at a Time" Treatment |
|---|---|---|
| sample 1 | 320 | 278 |
| sample 2 | 306 | 583 |
| sample 3 | 221 | 454 |
| sample 4 | 233 | 403 |
| sample 5 | 272 | 428 |
| sample 6 | 304 | 362 |
| sample 7 | 150 | 311 |
| sample 8 | 228 | 592 |
| sample 9 | 296 | 361 |
| sample 10 | 170 | 295 |
| Zero DNA | 0 | 0 |
| Mean GEU's | 250.0 | 406.7 |
| Standard Deviation | 56.2 | 105.1 |

EXAMPLE 4

Stable Transformation and Regeneration of Transgenic Plants

Several selection strategies were employed to isolate transgenic tissue. The first gene used was the antibiotic resistance gene hpt, which confers resistance to hygromycin. This gene was driven by the maize Ubi1 promoter. Whisker treated tissue was selected in liquid Ep media containing hygromycin B (Calbiochem-Novabiochem Corporation La Jolla, Calif. 92039-2087) at 25, 50, and 75 mg/l. The selection was applied after a recovery period of 0, 2, and 7 days. The high number of escapes obtained combined with the undesirability of antibiotic resistance in a production system for commercial product lead to a switch to the Bar gene, which confers resistance to the herbicide Bialaphos. Both Bialaphos and Herbiace™ (Meiji Seika Tokyo, Japan), a commercial herbicide preparation containing 20% Bialaphos, were used in stable experiments. Controls have survived on 0.25 mg/l and 0.5 mg/l Bialaphos, while no controls have grown out on 1.0 mg/l Bialaphos. Bialaphos selection was also done in liquid Ep media after a variety of recovery periods (0, 2, 3, 7, and 10 days were tried).

Stable transformants were obtained from whisker treated embryogenic cotton suspension lines under two different selection systems. The first transformant was selected on hygromycin. Treated tissue was placed in Ep media immediately after transformation. Selection at 25 mg/l was added seven days after that. The first pieces of growing tissue were isolated four weeks after the date of transformation. This line was later grown successfully on 50 mg/l hygromycin. Table 17 summarizes the transformation parameters used to obtain this transformant (#9–21).

TABLE 17

Summary of Treatment Parameters which Produced One Hygromycin Resistant Suspension Line (#9–21)

| | |
|---|---|
| Osmotic treatment | 4 hour pretreatment in Ep pLus 36.4 g/l mannitol and 36.4 g/l sorbitol |
| Tissue | C-49-B (genotype GC 510) 0.125 ml pcv/sample |
| DNA | 10 μg of p179-3 (SuperMas 1/GUS/nos) and 10 μg of Ubi/Hyg (DAS version) |
| Whiskers | 100 μl/sample of a 4% suspension of Advanced Composite whiskers |
| Agitation | 20 sec, Medium 2 speed on the Vari-Mix |
| Recovery Period | 7 days |
| Selection | 25 mg/l hygromycin |

Subsequent Southern analysis showed one hyrbridizing band confirming integration of the hygromycin resistance gene.

The second whisker transformed, embryogenic, cotton suspension line was selected on Herbiace™. Growing tissue was first isolated four weeks after transformation. Table 18 summarizes the transformation parameters for line #21-A. Histochemical GUS assay was positive after 11 weeks. Southern analysis confirmed the presence of GUS and bar genes. Plants were regenerated from the transformed embryogenic suspensions and were transferred to the greenhouse.

TABLE 18

Summary of Treatment Parameters which Produced One Herbiace ™ Resistant Suspension Line (#21-A)

| | |
|---|---|
| Osmotic treatment | 4 hour pretreatment in Ep plus 36.4 g/l mannitol and 36.4 g/l sorbitol |
| Tissue | 58-C-BY (genotype Coker 310) 0.125 ml pcv/sample |
| DNA | 20 μg of pDAB219 (35S/bar::35S/GUS) |
| Whiskers | 100 μl/sample of a 4% suspension of Advanced Composite whiskers |
| Agitation | 20 sec, Medium 2 speed on the Vari-Mix |

TABLE 18-continued

Summary of Treatment Parameters which
Produced One Herbiace ™ Resistant
Suspension Line (#21-A)

| | |
|---|---|
| Recovery Period | 3 days |
| Selection | 5.0 mg/l Herbiace |

Three more GUS positive suspension lines (#29-A, #30-A, and #30-B) were obtained, but have not yet been tested by Southern analysis. Tissue from line #29-A was isolated nine weeks after the date of transformation. A summary of experimental parameters is listed in Table 19. Lines #30-A and #30-B are from the same experiment (summarized in Table 20), but were isolated at different times. Line #30-A was isolated four and a half weeks after transformation and #30-B was isolated nine weeks after transformation. All transformed suspension lines have become well established and grow well in 5.0 mg/l Herbiace™. Lines #9–21 and #21-A have produced embryos and shoots.

TABLE 19

Summary of Treatment Parameters which
Produced Herbiace ™ Resistant
Suspension Line #29-A

| | |
|---|---|
| Osmotic treatment | 15 min pretreatment in Ep plus 12% sucrose |
| Tissue | 78-C-252 (genotype GC 510) 0.125 ml pcv/sample |
| DNA | 20 µg of pDAB219 (35S/bar::35S/GUS) |
| Whiskers | 100 µl/sample of a 4% suspension of Advanced Composite whiskers |
| Agitation | 20 sec, Medium 2 speed on the Vari-Mix |
| Recovery Period | 2 days |
| Selection | 5.0 mg/l Herbiace |

TABLE 20

Summary of Treatment Parameters which
Produced Herbiace ™ Resistant Suspension
Line #30-A and #30-B

| | |
|---|---|
| Osmotic treatment | 15 min pretreatment in Ep plus 12% sucrose |
| Tissue | 58-C-BY (genotype Coker 310) 0.125 ml pcv/sample |
| DNA | 20 µg of pDAB219 (35S/bar::35S/GUS) |
| Whiskers | 100 µl/ sample of a 4% suspension of Advanced Composite whiskers |

TABLE 20-continued

Summary of Treatment Parameters which
Produced Herbiace ™ Resistant Suspension
Line #30-A and #30-B

| | |
|---|---|
| Agitation | 20 sec, Medium 2 speed on the Vari-Mix |
| Recovery Period | 3 days |
| Selection | 5.0 mg/l Herbiace |

Southern Blot Analysis

Genomic DNA from callus was extracted from lyophilized tissue using DNEASY Plant Kit (Qiagen Inc., Chatsworth, Calif., USA). Five micrograms of cotton DNA samples were digested with EcoR I (NEB, Beverly, Miss., USA). The digested DNA was loaded onto a 0.85% SeaKem LE agarose (FMC, Rockland, Me., USA) gel and electrophoresed overnight. The gel was blotted onto a Millipore Immobilon-Ny+(Bedford, Miss., USA) membrane overnight in 20×SSC. DNA fragments specific to GUS coding region and BAR coding region were isolated from plasmid pDAB219, using restriction enzymes Nco I/Sac I and Pst I/Bgl I (NEB, Beverly, Miss., USA). These fragments were purified using the QIAEX II DNA purification kit (Qiagen Inc., Chatsworth, Calif., USA). The probes were labeled with ($\alpha^{32}$P dCTP (Amersham Life Science, Arlington Heights, Ill., USA) using the Stratagene PRIME IT RmT dCTP Labeling Reaction Kit (La Jolla, Calif., USA) and used for hybridization (southern 1975, 1980). After hybridization, the membranes were washed in 0.1×SSC and 0.1% SDA for 30 min at 60° C. and exposed to HYPERFILM MP X-ray films (Amershan Life Sciences, Arlington Heights, Ill., USA), using a BIOMAX TRANSCREEN-HE intensifying screen (Eastman Kodak Company, Rochester, N.Y., USA). The films were developed in SRX-101 film processor (Konica, Wayne, N.J., USA) after overnight exposure at −70° C.

Southern hybridization results indicated that all four putative transgenic cotton suspension lines (21-C-5; 219-29-A; 219-30-A and 219-30-B) had intact GUS and BAR transgene.

The invention claimed is:

1. A method for transforming a cotton cell in an embryogenic cotton suspension culture which comprises: inserting DNA into said cell by whisker mediated transformation.

\* \* \* \* \*